United States Patent
Yarnykh et al.

(10) Patent No.: US 7,315,756 B2
(45) Date of Patent: Jan. 1, 2008

(54) MULTI-SLICE DOUBLE INVERSION-RECOVERY BLACK-BLOOD IMAGING WITH SIMULTANEOUS SLICE RE-INVERSION

(75) Inventors: Vasily L. Yarnykh, Seattle, WA (US); Chun Yuan, Bellevue, WA (US)

(73) Assignee: University of Washington, Seattle, WA (US)

( * ) Notice: Subject to any disclaimer, the term of this patent is extended or adjusted under 35 U.S.C. 154(b) by 667 days.

(21) Appl. No.: 10/788,937

(22) Filed: Feb. 27, 2004

(65) Prior Publication Data
US 2004/0181146 A1    Sep. 16, 2004

Related U.S. Application Data

(60) Provisional application No. 60/452,071, filed on Mar. 3, 2003.

(51) Int. Cl.
*A61B 5/05* (2006.01)
(52) U.S. Cl. .................. 600/411; 600/410; 600/419; 324/306; 324/307; 324/309
(58) Field of Classification Search .............. 600/410, 600/411, 419; 324/306, 307, 309
See application file for complete search history.

(56) References Cited

U.S. PATENT DOCUMENTS 6,498,946 B1 * 12/2002 Foo et al. .................. 600/410

OTHER PUBLICATIONS

Fayad et al. Noninvasive In Vivo Human Coronary Artery Lumen and Wall Imaging Using Black Blood Magnetic Resonance Imaging. Circulation. 102: pp. 506-510. 2000.*

Kholmovski et al. A Generalized k-Sampling Scheme for 3D Fast Spin Echo. Journal of Magnetic Resonance Imaging. 11: pp. 549-558. 2000.*

Bonk, Schmiedl, Yuan, Nelson, Black, and Ladd. "Time-of-Flight MR Angiography With Gd-DTPA Hexamethylene Diamine Co-Polymer Blood Pool Contrast Agent: Comparison of Enhanced MRA and Conventional Angiography for Arterial Stenosis Induced in Rabbits." *Journal of Magnetic Resonance Imaging*, 11:638-646 2000. © 2000 Wiley-Liss, Inc. pp. 638-646.

Cai, Hatsukami, Ferguson, Small, Polissar, and Yuan. "Classification of Human Carotid Atherosclerotic Lesions With In Vivo Multicontrast Magnetic Resonance Imaging." *Circulation, Journal of the American Heart Association*, Sep. 10, 2002, pp. 1368-1373.

(Continued)

*Primary Examiner*—Brian L. Casler
*Assistant Examiner*—Parikha S. Mehta
(74) *Attorney, Agent, or Firm*—Ronald M. Anderson (57) ABSTRACT

A multi-slice double inversion recovery (DIR) pulse sequence with read out of a signal for imaging successive slices implemented on a magnetic resonance image scanner. In the method, when the DIR pulse sequence is applied before imaging each slice, a slab-selective inversion re-inverts the entire slab that includes all of the slices. All slices are imaged within a predefined repetition time (TR). The number, N, of slices acquired per TR controls the inversion time to execute the read out of the signal for imaging each slice at a zero-crossing point of blood. In a test, multi-slice DIR images of carotid arteries were obtained with N ranging from 2-8, for four subjects. The results were compared with those for both standard single-slice DIR, and inflow saturation techniques. Multi-slice DIR with N=2-6 provided blood flow suppression in carotid arteries similar to that of single-slice DIR, and significantly better than inflow saturation.

44 Claims, 4 Drawing Sheets

OTHER PUBLICATIONS

Chu, Kampshulte, Ferguson, Kerwin, Yarnykh, O'Brien, Polissar, Hatsukami, and Yuan. "Occurrence and Staging of Hemorrhage in the Advanced Carotid Atherosclerotic Plaque: An In-Vivo Multi Contrast High Resolution MRI Study." Submitted to *Stroke*, Oct. 2003. 25pp.

Winn, Schmiedl, Reichenbach, Beach, Nghiem, Dimas, Daniel, Maravilla, and Yuan. "Detection and Characterization of Atherosclerotic Fibrous Caps with T2-Weighted MR." *AJNR Am J Neuroadiol* 19:129-134, Jan. 1998, pp. 129-164.

Xu, Hwang, and Yuan. "Segmentation of Multi-Channel Image with Markov Random Field Based Active Contour Model." © luwer Academic Publishers, The Netherlands 2002. Accepted Aug. 7, 2001. 11pp.

Yarnykh and Yuan. "High-Resolution Multi-Contrast MRI of the Carotid Artery Wall for Evaluation of Atherosclerotic Plaques." *Current Protocols in Magnetic Resonance Imaging*, Unit A1.4, Intracranial Arterial Disease. Supplement 11. 2003. 18pp.

Yarnykh and Yuan. "Multislice Double Inversion-Recovery Black-Blood Imaging With Simultaneous Slice Reinversion." *Journal of Magnetic Resonance Imaging*, 17:478-483 (2003). pp. 478-483.

Yarnykh, Vasily L. "Pulsed Z-Spectroscopic Imaging of Cross-Relaxation Parameters in Tissues for Human MRI: Theory and Clinical Applications." *Magnetic Resonance in Medicine*, 47:929-939 (2002). pp. 929-939.

Yuan, Beach, Smith, and Hatsukami. "Measurement of Atherosclerotic Carotid Plaque Size in Vivo Using High Resolution Magnetic Resonance Imaging." *Circulation, Journal of the American Heart Association*. Dec. 15, 1998. pp. 2666-2671.

Yuan, Hatsukami, and O'Brien. "High-Resolution Magnetic Resonance Imaging of Normal and Atherosclerotic Human Coronary Arteries Ex Vivo: Discrimination of Plaque Tissue Components." *MRI of Human Coronary Arteries*, vol. 49, No. 6, Nov. 2001. pp. 491-499.

Yuan, Kerwin, Ferguson, Polissar, Zhang, Cai, and Hatsukami. "Contrast-Enhanced High Resolution MRI for Atherosclerotic Carotid Artery Tissue Characterization." *Journal of Magnetic Resonance Imaging*, 15:62-67 (2002). pp. 62-67.

Yuan, Lin, Millard, and Hwang. "Closed Contour Edge Detection of Blood Vessel Lumen and Outer Wall Boundaries in Black-Blood MR Images." *Magnetic Resonance Imaging*, vol. 17, No. 2, 1999. pp. 257-266.

Yuan, Miller, Cai, and Hatsukami. "Carotid atherosclerotic wall imaging by MRI." *Neuroimaging Clinics of North America*, 12 (2002). pp. 391-401.

Yuan, Mitsumori, Beach, and Maravilla. "Carotid Atherosclerotic Plaque: Noninvasive MR Characterization and Identification of Vulnerable Lesions." *Radiology*, vol. 221, No. 2, Nov. 2001. pp. 285-299.

Yuan, Mitsumori, Ferguson, Polissar, Echelard, Ortiz, Small, Davies, Kerwin, and Hatsukami. "In Vivo Accuracy of Multispectral Magnetic Resonance Imaging for Identifying Lipid-Rich Necrotic Cores and Intraplaque Hemorrhage in Advanced Human Carotid Plaques." *Circulation, Journal of the American Heart Association*, Oct. 23, 2001. pp. 2051-2056.

Yuan, Zhang, Polissar, Ehelard, Ortiz, Davis, Ellington, Ferguson, and Hatsukami. "Identification of Fibrous Cap Rupture With Magnetic Resonance Imaging Is Highly Associated With Recent Transient Ischemic Attack or Stroke." *Circulation, Journal of the American Heart Association*, Jan. 16, 2002. pp. 181-185.

Yuan, Zhao, and Hatsukami. "Quantitative Evaluation of Carotid Atherosclerotic Plaques by Magnetic Resonance Imaging." *Current Atherosclerosis Reports 2002*, vol. 4. © 2002 Current Sciences Inc. pp. 351-357.

Zhang, Cai, Luo, Han, Polissar, Hatsukami, and Yuan. "Measurement of Carotid Wall Volume and Maximum Area with Contrast-enhanced 3D MR Imaging: Initial Observations." *Radiology*, vol. 228, No. 1, Jul. 2003. pp. 200-205.

Zhang, Hatsukami, Polissar, Han, and Yuan. "Comparison of carotid vessel wall area measurements using three difference contrast-weighted black blood MR imaging techniques." *Magnetic Resonance Imaging*, 19 (2001) pp. 795-802.

Zhao, Yuan, Hatsukami, Frechette, Kang, Maravilla, and Brown. "Effects of Prolonged Intensive Lipid-Lowering Therapy on the Characteristics of Carotid Artheroscleotic Plaques In Vivo by MRI, A Case-Control Study." *Arterioscler Thromb Vasc Biol*. Oct. 2001. pp. 1623-1629.

Kerwin, Hooker, Spilker, Vicini, Ferguson, Katsukami, and Yuan. "Quantitative Magnetic Resonance Imaging Analysis of Neovasculature Volume in Carotid Atherosclerotic Plaque." *Circulation, Journal of the American Heart Association*, Feb. 18, 2003. pp. 851-856.

Miller and Yuan. "Atherosclerotic Plaque Imaging Techniques in Magnetic Resonance Images." *Angiography and Plaque Imaging, Advanced Segmentation Techniques*. The Biomedical Engineering Series, Michael Neuman, Series Editor. CRC Press, Boca Raton, FL. Chapter 7. pp. 299-320, no date.

Mitsumori, Hatsukami, Ferguson, Kerwin, Cai, and Yuan. "In Vivo Accuracy of Multisequence MR Imaging for Identifying Unstable Fibrous Caps in Advanced Human Carotid Plaques." *Journal of Magnetic Resonance Imaging*, 17:410-420 (2003). pp. 410-420.

Naghavi, Morteza et al. "From Vulnerable Plaque to Vulnerable Patient, A Call for New Definitions and Risk Assessment Strategies: Part I." *Circulation, Journal of the American Heart Association*, Oct. 7, 2003. pp. 1664-1672.

Naghavi, Morteza et al. "From Vulnerable Plaque to Vulnerable Patient, A Call for New Definitions and Risk Assessment Strategies: Part II." *Circulation, Journal of the American Heart Association*, Oct. 14, 2003. pp. 1772-1778.

Saam and Yuan. "Vascular Imaging." *Encyclopedia of Biomaterials and Biomedical engineering*. Oct. 2003. 26pp.

Saam et al. In Vivo Comparison of the Atherosclerotic Lesion Ipsilateral and Contralateral to the Side of Symptomatic Carotid Disease: A High-Resolution, Multi-Contrast Magnetic Resonance Imaging Study. Submitted to *Stroke*, Oct. 2003. 25pp.

Saam, Cai JM, Cai YQ, Ma, Xu, Polissar, Hatsukami, and Yuan. "Differences in Carotid Artery Atherosclerotic Lesion Characteristics from the Index- and Non-Index Side of Symptomatic Patients: A High-Resolution, Multi Contrast Magnetic Resonance Imaging Study." Submitted to *Stroke*, Oct. 2003. 19pp.

Schwartz, Hatsukami, and Yuan. "Molecular Markers, Fibrous Cap Rupture, and the Vulnerable Plaque, New Experimental Opportunities." *Circulation, Journal of the American Heart Association*, Sep. 14, 2001. pp. 471-473.

Han and Yuan. "Plaque Morphological Quantitation." *Angiography and Plaque Imaging, Advanced Segmentation Techniques*. Chapter 2. The Biomedical Engineering Series, Michael Neuman, Series Editor. CRC Press, Boca Raton, FL. pp. 43-76, no date.

Han, Hatsukami, and Yuan. "A Multi-Scale Method for Automatic Correction of Intensity Non-Uniformity in MR Images." *Journal of Magnetic Resonance Imaging*, 13:428-436 (2001). (2) Wily-Liss, Inc.

Han, Hatsukami, Hwang, and Yuan. "A Fast Minimal Path Active Contour Model." *IEEE Transactions On Image Processing*, vol. 10, No. 6, Jun. 2001. pp. 865-873.

Han, Kerwin, Hatsukami, Hwang, and Yuan. "Detecting Objects in Image Sequences Using Rule-Based Control in an Active Contour Model." *IEEE Transaction on Biomedical Engineering*, vol. 50, No. 6, Jun. 2003. pp. 705-710.

Hatsukami, Ross, Polissar, and Yuan. "Visualization of Fibrous Cap Thickness and Rupture in Human Atherosclerotic Carotid Plaque In Vivo With High-Resoluation Magnetic Resonance Imaging." *Circulation, Journal of the American Heart Association*. Aug. 29, 2000. pp. 959-964.

Kaneko, Skinner, Raines, Yuan, Rosenfeld, Wight, and Ross. "Detection of dissection and remodeling of atherosclerotic lesions in rabbits after balloon angioplasty by magnetic-resonance imaging." *Coronary Artery Disease*, Diagnostic Methods, 2000, vol. 11 No. 8.

Kang, Polissar, Han, Lin, and Yuan. "Analysis of the Measurement Precision of Arterial Lumen and Wall Areas Using High-Resolution MRI." Measurement Precision of High-Resolution MRI. *Magnetic Resonance in Medicine*, 44:968-972 (2000). pp. 968-972.

Kerwin and Yuan. "Analysis And Visualization Of Athersclerotic Plaque Composition By MRI." *Angiography and Plaque Imaging*,

*Advanced Segmentation Techniques.* The Biomedical Engineering Series, Michael Neuman, Series Editor. CRC Press, Boca Raton, FL. Chapter 3. pp. 77-117, no date.

Kerwin, Cai, and Yuan. "Noise and Motion Correction in Dynamic Contrast-Enhanced MRI for Analysis for Atherosclerotic Lesions." *Magnetic Resonance in Medicine*, 47:1211-1217 (2002). pp. 1211-1217.

Kerwin, Han, Chu, Xu, Luo, Hwang, Hatsukami, and Yuan. "A Quantitative Vascular Analysis System for Evaluation of Athersclerotic Lesions by MRI." Medical Image Computing and Computer-Assisted Intervention—MICCAI 2001, 4th International Conference Utrecht, The Netherlands, Oct. 2001 Proceedings. Niessen and Viergever, eds. 9pp.

Parker, Dennis L., K. Craig Goodrich, Marilyn Masiker, Jay S. Tsuruda, and Gregory L. Katzman. "Improved Efficiency in Double-Inversion Fast Spin-Echo Imaging," *Magnetic Resonance Medicine* 2002, 47:1017-1021.

Song, H.K. "Highly Efficient Double-Inversion Spiral Technique for Coronary Vessel Wall Imaging," *Proceedings of the 10th Annual Meeting of ISMRM*, Honolulu, 2002, p. 1566.

Song H.K., Alexander C. Wright, Ronald, L. Wold, and Felix W. Wehrli. "Multislice Double Inversion Pulse Sequence for Efficient Black-Blood MRI" *Magnetic Resonance Medicine* 2002, 47:616-620.

* cited by examiner

MULTI-SLICE DOUBLE INVERSION-RECOVERY BLACK-BLOOD IMAGING WITH SIMULTANEOUS SLICE RE-INVERSION

RELATED APPLICATIONS

This application is based on copending provisional patent application Ser. No. 60/452,071, filed Mar. 3, 2003, the benefit of the filing date of which is hereby claimed under 35 U.S.C. § 119(e).

GOVERNMENT RIGHTS

This invention was made with government support under Grant No. RO1-HL56874, awarded by NIH-NIHBI, and the federal government may have certain rights in this invention.

FIELD OF THE INVENTION

This invention generally pertains to magnetic resonance imaging (MRI) and more specifically, pertains to a method and a system that use a plurality of radio frequency (RF) inversion pulses grouped into double-inversion procedures in order to suppress the signal from flowing blood when imaging a plurality of slices, while performing a simultaneous slab-selective re-inversion, wherein the slab includes the plurality of slices being imaged.

BACKGROUND OF THE INVENTION

Efficient suppression of the signal from flowing blood is especially important for cardiovascular MRI, where anatomic structures and pathologic tissues of interest are close to blood, and flow artifacts may cause severe problems for diagnostic interpretation. Blood-suppressed (black-blood) imaging is currently based on two well-known techniques: in-flow saturation (see Edelman, R. R. et al., "Extracranial carotid arteries: evaluation with "black blood" MR angiography," *Radiology* 1990, 177:45-50; and Steinman, D. A. et al., "On the nature and reduction of plaque mimicking flow artifacts in black blood MRI of the carotid bifurcation," *Magnetic Resonance Medicine* 1998, 39:635-641), and double inversion-recovery (DIR) (see Edelman, R. R. et al., "Fast selective black blood MR imaging," *Radiology* 1991, 181:655-660; and Simonetti, O. P. et al., "Black blood T2-weighted inversion recovery MR imaging of the heart," *Radiology* 1996, 199:49-57). The method of in-flow saturation usually does not enable complete elimination of the signal from flowing blood and may be ineffective in applications that require clear visualization of the interface between vessel wall and lumen, such as high-resolution imaging of atherosclerotic plaque. The DIR technique is known, to date, as one of the more effective black-blood imaging modalities. The principle of DIR is that the signal from all spins within a transmit coil volume is inverted by a non-selective 180° pulse, which is followed by a slice-selective 180° pulse to restore the magnetization of a slice that is about to be imaged. After a properly chosen inversion time (TI), the magnetization of inflowing blood achieves a zero-crossing point, so that the observed signal does not contain a contribution from blood. Thus, DIR provides two general advantages: (1) it has the potential to completely eliminate the signal from flowing blood; and, (2) it has minimal sensitivity to the blood flow rate, which, in fact, should guarantee only the outflow from a relatively thin imaged slice. However, DIR, as used in this manner, is essentially applicable to imaging only a single slice per repetition time (TR), and therefore, a long scan time is required if several slices need to be imaged using the DIR method.

To improve the time efficiency of DIR, two multi-slice acquisition strategies were recently proposed. Song et al., as reported in "Multislice double inversion pulse sequence for efficient black-blood MRI," *Magnetic Resonance Medicine* 2002, 47:616-620, developed a double-slice technique that uses one non-selective and two consecutive slice-selective inversions. Following the TI period, fast spin-echo (FSE) readouts are then applied consecutively to the corresponding slices to acquire the signals for imaging the slices. With this approach, only the signal for imaging one slice can be acquired at the moment of zeroing blood magnetization, while the acquisition of the signal for imaging the second slice is delayed from the zero-crossing point of the blood magnetization by the duration of the readout process. Any further increase in the number of slices acquired within one repetition time (TR) requires a shorter readout sequence to be used to minimize the effect of flowing blood. A five-slice extension of this technique was recently demonstrated with spiral readout by Song et al. (see "Highly efficient double-inversion spiral technique for coronary vessel wall imaging," *Proceedings of the 10th Annual Meeting of ISMRM*, Honolulu, 2002, p. 1566). However, the use of a relatively long FSE readout sequence, which is preferable in most applications due to image quality and tissue contrast, may preclude an increase in the number of slices per TR. Parker et al. (see "Improved efficiency in double-inversion fast spin-echo imaging," *Magnetic Resonance Medicine* 2002, 47:1017-1021) proposed an alternative method that enables acquisition of each slice at the exact zero-crossing point. In this technique, the slices are acquired sequentially within the TR, while TI is reduced. This method results in several zero-crossing points per TR, each for the corresponding slice. Similar to the method of Song et al., a preparative module in the method of Parker et al. consists of a non-selective inversion followed by a train of slice-selective inversions applied successively to the slices to be imaged within one TR. The method was demonstrated in two- and four-slice variants. The four-slice technique, however, was implemented with a doubled TR that resulted in the same time efficiency as the two-slice procedure.

A common problem of the above-noted multi-slice DIR techniques is the construction of a preparative module, which includes a train of slice-selective inversions, creating unequal conditions for the evolution of magnetization of different slices, since the delay between non-selective inversion and slice-selective re-inversion depends on the actual slice number. Furthermore, the restrictions on specific absorption rate (SAR) also may preclude a further increase of slice quantity. It is especially critical for the method of Parker et al., in which the number of slice-selective inversion pulses per TR is equal to the square of the number of slices, where for example, 16 inversions should be applied for four-slice imaging.

To overcome this problem, it would be desirable to develop an alternative multi-slice DIR technique that is based on the simultaneous re-inversion of a group of slices. Such a technique should provide the required time efficiency without the problems of the prior art, while enabling the signal for imaging each successive slice to be acquired at the time the contribution to the signal from flowing blood is substantially zero or approaching zero.

SUMMARY OF THE INVENTION

In accord with the present invention, a method is defined for suppressing a contribution from flowing blood to a signal used for MRI of each of a plurality of slices at a site in a patient, within a predefined repetition time. The method includes the step of applying a non-selective inversion RF pulse and a selective inversion RF pulse in either order. In this method, the selective inversion RF pulse simultaneously inverts a magnetization for all of the plurality of slices that are to be imaged at the site within the predefined repetition time. After waiting a predefined inversion time or TI, which is calculated as a function of a number of slices to be imaged at the site, a sequence of RF pulses and magnetic field gradient pulses is executed to read out a signal for imaging a selected single slice from the plurality of slices. Then, after a predefined delay time that is also calculated as a function of the number of slices to be imaged, these steps are repeated to image each of the plurality of slices in succession. The method further includes the step of storing the signal read out for each successive slice to enable a discrete image of each successive slice to be selectively displayed when desired.

The predefined TI and the predefined delay time are determined so that the sequence of RF pulses and magnetic field gradient pulses are applied to read out the signal for imaging each selected single slice at a time when the magnetization signal for the flowing blood is substantially zero. Since a benefit of the present invention is suppressing the contribution of flowing blood to the signals used for imaging the successive slices, the site of the imaging will normally include at least one artery conveying flowing blood.

Another aspect of the present invention is directed to a memory medium on which machine executable instructions are stored for carrying out the steps of the method described above.

Yet another aspect of the present invention is directed to a system for multi-slice double-inversion recovery black-blood imaging. The system includes an MRI apparatus adapted for producing an image of a site, and a computer coupled to the MRI apparatus to control it. The computer includes a memory in which machine instructions are stored, and a processor that is coupled to the memory for executing the machine instructions to control the MRI apparatus and carry out a sequence of operations. These operations generally correspond to the steps of the method described above.

Still another aspect of the present invention is directed to a pulse sequence for multi-slice DIR magnetic resonance imaging. This pulse sequence includes pulse components generally in accord with the method discussed above.

Yet another aspect of the present invention is directed to a method for enabling visual evaluation of atherosclerotic plaque at a site in a patient. This method is similar to the method noted above, but in addition, repeats all of the steps for each of a plurality of transverse slices at the site being imaged. The plurality of transverse slices is within planes that are generally transverse relative to the plurality of slices initially imaged to provide a reference when acquiring the signals for imaging the transverse slices. In addition, the method includes the step of displaying selected transverse slices of the site, so that any atherosclerotic plaque formation in an artery of the patient at the site is clearly visible. A contribution due to flowing blood in each transverse slice is thus suppressed to more clearly visually display any atherosclerotic plaque formation in an artery at the site.

Still another aspect of the invention pertains to a method for fast black-blood angiography, wherein the steps described above are used to acquire a plurality of images corresponding to a plurality of slices that are disposed in an oblique plane along the longitudinal direction of a blood vessel. Such images depict fragments of blood vessels as being consistently dark compared to surrounding tissues and any pathologic lesions inside the vessels such as the atherosclerotic plaque or the thrombus. A plurality of oblique black-blood images is then processed by multi-planar reformation or minimal intensity projection in order to enable the vascular anatomy to be clearly visible.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

Principle of Multi-Slice DIR Acquisition

Figure 1:
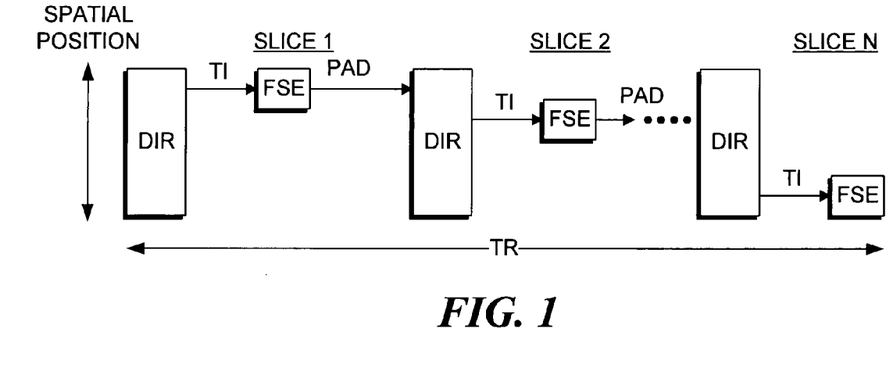
FIG. 1 is a schematic functional diagram of a slice acquisition scheme for a multi-slice DIR-FSE sequence.

A schematic functional diagram of a multi-slice DIR-FSE sequence in accord with the novel method described herein is shown in FIG. 1. In FIG. 1, slices are imaged sequentially within the TR, as shown by FSE readout blocks. A DIR preparation is executed before read out of each slice. Each DIR block includes a slab-selective inversion applied to an entire slice pack. The proper timing of the sequence is controlled by a post-acquisition delay (PAD), which allows for coincidence of the zero-crossing point of blood (see Eq. [1] below) and the start of an FSE readout. The general idea of this method is to replace a slice-selective inversion in the DIR preparation by a slab-selective one, which is applied to an entire slab of slices to be imaged within a TR. The DIR sequence is repeated for each slice, while a shortened TI provides imaging of several slices per TR. A predefined post-acquisition delay (referred to as "PAD" in FIG. 1) is used after an echo pulse train for acquiring the signal to image a slice, to provide an adjustment so that there are equal time intervals between non-selective inversion pulses. With these conditions, the magnetization of inflowing blood equals or approaches zero at:

$$TI(N) = -T_1 \ln(0.5(1 + \exp(-TR/T_1 N))) \quad [1]$$

where N is the number of slices per TR, and $T_1 = 1200$ ms in blood. The TI values corresponding to different values of N at TR=2500 ms are given below in Table 1.

TABLE 1

Comparison between Multi-Slice DIR-FSE Scans with Variable Number of Slices per TR (N)

| N | TI(N)[a] ms | SNR in carotid arteries ± SD | P for SNR in carotid arteries as compared to N = 1[b] | SI(N)/SI(1)[c] in muscle | $V_{min}$ cm/s[d] |
|---|---|---|---|---|---|
| 1 | 691 | 1.36 ± 0.17 | — | 1 | 0.6 |
| 2 | 469 | 1.39 ± 0.24 | 0.34 | 0.91 | 1.6 |
| 3 | 346 | 1.39 ± 0.29 | 0.62 | 0.82 | 3.3 |
| 4 | 272 | 1.46 ± 0.21 | 0.10 | 0.75 | 5.7 |
| 5 | 224 | 1.47 ± 0.23 | 0.06 | 0.68 | 8.6 |
| 6 | 190 | 1.45 ± 0.24 | 0.11 | 0.64 | 12.2 |
| 8 | 146 | 1.63 ± 0.24 | 0.0004 | 0.51 | 21.1 |
| 8[e] | — | 2.18 ± 0.28[e] | <0.0001[e] | 0.76[e] | — |

[a]Calculated by Eq. [1].
[b]By paired Student's t-test.
[c]Signal intensities for multi-slice scans normalized to a signal intensity for the single-slice scan.
[d]Calculated by Eq. [2].
[e]Data for the FSE sequence with inflow saturation.

Subjects

Three healthy volunteers (ages 22, 57, and 58 years, including two males and one female), and one carotid atherosclerosis patient (a 60 year-old female) with a 50 percent stenosis participated in this study. Informed consent was obtained from all participants. The study was performed in compliance with the requirements of the institutional review board.

MRI Experiments

The multi-slice DIR pulse sequence was implemented on a 1.5T MR scanner (Signa Horizon EchoSpeed 5.8™, made by General Electric Co., Milwaukee, Wis.) in combination with an FSE readout. A double-inversion block consisted of a 0.8 ms rectangular non-selective pulse, and a slice-selective adiabatic hyperbolic-secant pulse with a duration of 8.64 ms. Optionally, both the non-selective and slice selective pulses can be adiabatic inversion RF pulses. The thickness of a re-inverted slab was twice the thickness of an imaged slice pack to guarantee uniform re-inversion for all slices. All scans were obtained with a custom designed, surface phased-array coil for carotid imaging. It will be apparent that other types of MRI apparatus and other methods for acquiring the signals used to image successive slices can alternatively be used in accord with the present invention.

To test flow suppression and image quality provided by the multi-slice DIR technique, PD-weighted black-blood images of cervical carotid arteries were obtained from three healthy volunteers, for N ranging from 1 to 8 (see Table 1). The common parameters for all scans were: TR 2500 ms, TE 9 ms, echo train 12, NEX 2, matrix 256×256, FOV 14×10 cm, slice thickness 2 mm, receiver bandwidth 31 kHz, scan time about 1.5 min per each of N slices. Within each scan corresponding to the specified N value, from four to twelve images were acquired to cover bilateral carotid bifurcations and adjacent segments of carotid arteries. TI were calculated by Eq. [1] and varied between 146 ms for N=8 and 690 ms for N=1 (see Table 1, supra). Additionally, an FSE scan, with inferior and superior flow pre-saturation and with the same parameters of an imaging sequence, was acquired for each volunteer.

The signal-to-noise ratios (SNR) in the lumina of bilateral common, internal, and external carotid arteries at matched locations (a total of 42 measurements per N value) were compared among the protocols using paired student's t-test. To estimate saturation of steady tissues, the signal intensities (SI) in neck muscles were measured and normalized to the intensities for single-slice scan, SI(1). In one volunteer, the multi-slice DIR technique was tested to obtain $T_2$-weighted images with TR/TE/TI=2500/50/272 ms, respectively, and N=4. In an atherosclerosis patient, PD-weighted images were compared between the DIR techniques with N=1 and N=4.

Results

Figure 2:
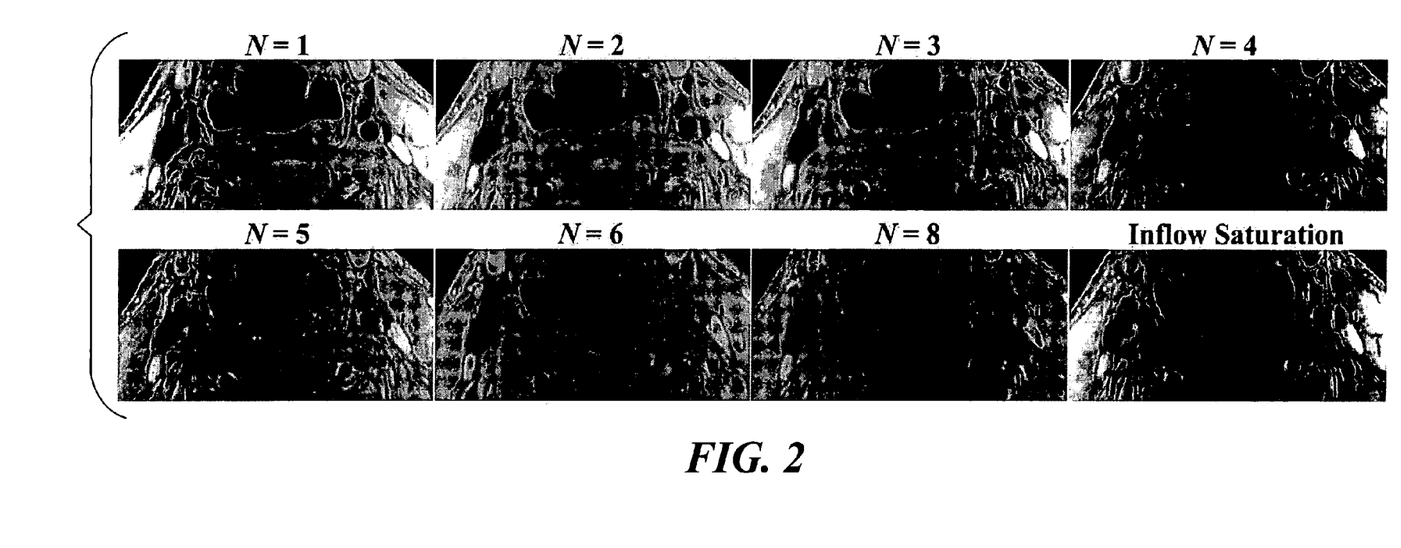
FIG. 2 illustrates a plurality of proton density (PD)-weighted images of neck vasculature obtained from a healthy volunteer using multi-slice DIR-FSE sequence with variable number (N) of slices per TR, and for comparison, an image obtained using the FSE sequence with inflow saturation.
Figure 3:
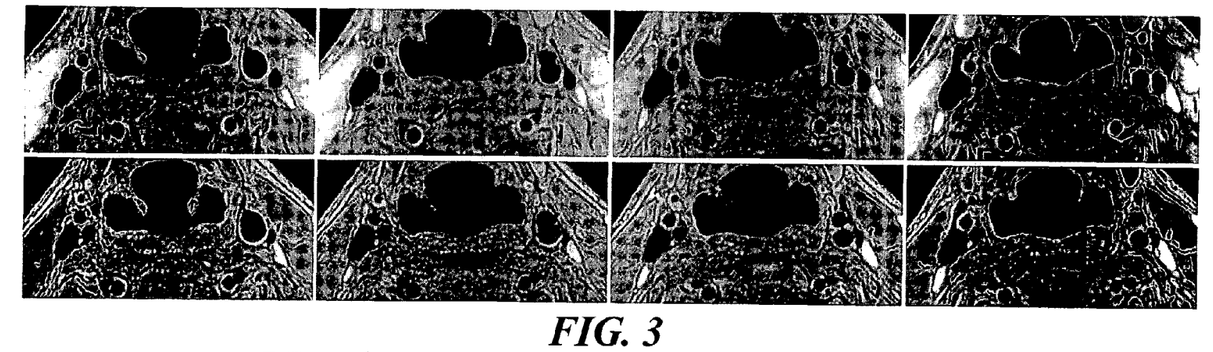
FIG. 3 illustrates a plurality of multi-slice DIR-FSE images of neck vasculature with the acquisition of the signal for four slices per TR (TR/TI=2500/272 ms, N=4), for the same volunteer as in FIG. 2, wherein the top row includes PD-weighted images (echo time (TE)=9 ms), and the bottom row includes $T_2$-weighted images (TE=50 ms), with an acquisition time for each image of about 1.5 min.
Figure 4:
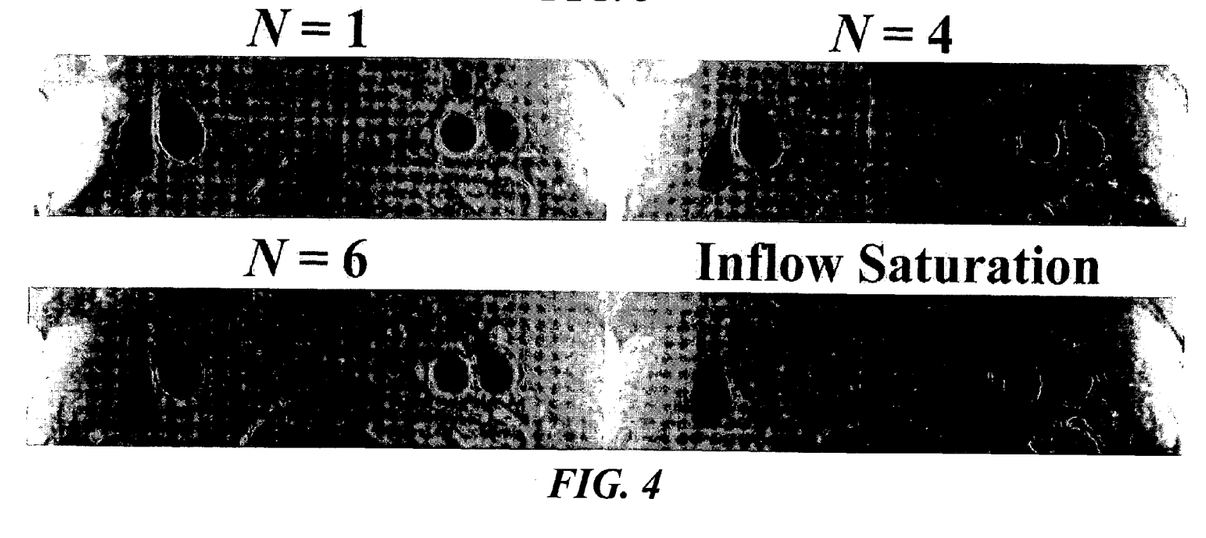
FIG. 4 illustrates a plurality of images comparing blood suppression in the carotid bifurcation by the multi-slice DIR-FSE sequence with variable number of slices per TR (N) and the FSE sequence with inflow saturation, wherein PD-weighted images of neck vasculature were obtained from a healthy volunteer.
Figure 5:
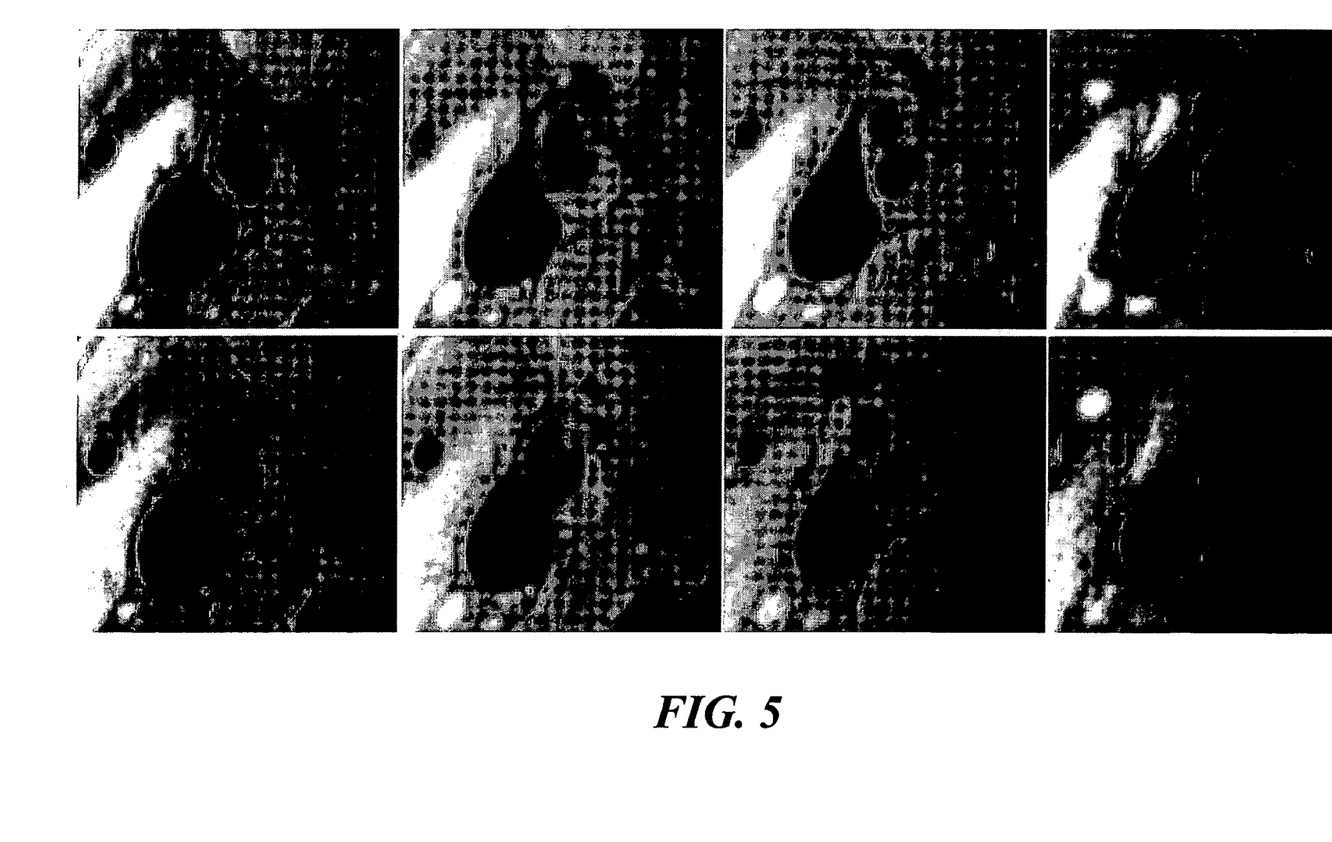
FIG. 5 illustrates four consecutive PD-weighted DIR-FSE images of the right carotid artery obtained from an atherosclerosis patient with a 50 percent stenosis, wherein the top row is produced using a single-slice technique, and the bottom row is produced using a four-slice technique.

FIGS. 2-5 demonstrate typical images obtained using the multi-slice DIR method of this invention. In FIGS. 2 and 4, the images acquired with a different number of slices per TR are shown for the identical anatomic locations. The results of image analysis are summarized above in Table 1. The images did not show significant differences in SNR values in carotid arteries between DIR scans with N=1-6. At N=8, suppression of arterial flow became slightly compromised. Also, the residual flow signal in some veins increased visibly, starting from N=4-6. It is noticeable that at all N, multi-slice DIR provided significantly better blood flow suppression than inflow saturation. This effect is clearly seen at the bifurcation level in FIG. 4. A minor residual flow signal in the left jugular vein is seen only at N=6.

While comparing the multi-slice DIR scans with variable N, it was determined that the signal from stationary tissues decreased progressively with an increase of N (see FIG. 2 and Table 1). As seen from the quantitative data on the signal intensities in muscle tissue (Table 1), at the identical N=8, multi-slice DIR produces considerably lower signal than FSE with inflow-saturation. This finding reveals that multiple DIR preparative modules deliver extra saturation of stationary tissues relative to the multi-slice FSE sequence alone. However, up to N=4, image quality remained sufficient for clear delineation of the vessel wall on both PD- and $T_2$-weighted images (see FIG. 3).

In a clinical example (shown in FIG. 5), standard single-slice DIR and the method of the invention described herein provided similar image quality and visualization of atherosclerotic plaque, with N=4. A complex plaque is seen at the bifurcation level. Both techniques show identical appearance of the plaque except for a minor misregistration between the image sets.

Discussion

The described method represents an alternative technical solution to add a multi-slice capability to the use of DIR for flowing blood suppression. In contrast to the prior art multi-slice DIR techniques, the present method was tested for a wide range of slice quantities, N, acquired per TR. The results show that the present multi-slice DIR technique can be applied and will provide a reasonable quality of flow suppression for blood, even when the signals for imaging eight slices are acquired per TR. It is worth noting that comparable time efficiency is technically unachievable while using prior art methods. For instance, the eight-slice implementation of the method of Song et al. with 12 echoes in a train and the shortest available echo spacing (about 7 ms) would result in about 700 ms delay between an acquisition of the first and the last slice, leading to considerable relaxation of the blood signal (i.e., deviation from the zero crossing point) by the time the last slices are imaged. In the technique of Parker et al., a similar time efficiency would require an impractically large number of slice-selective inversions, i.e., 64 per TR.

It was determined in these tests that flow suppression becomes slightly compromised with an increase in the number of slices. This effect was expected, because flowing blood suppression by DIR presumes complete outflow from an imaged slice during TI. Clearly, this requirement limits the available number of slices per TR, since an increase of N leads to an increase in slab thickness and a decrease of TI (see Eq. [1]). One purpose of this study was to estimate how significant the increase of flow sensitivity is in the present method, from a statistical point of view. As seen from the Results section provided above, for a particular set of pulse sequence parameters, multi-slice DIR with up to six slices per TR provided almost the same efficiency of flowing blood suppression in carotid arteries as standard single-slice DIR. Obviously, the slow venous flow appeared to be more difficult to suppress completely using this technique with large N.

To characterize flow sensitivity of multi-slice DIR quantitatively, it is convenient to introduce a parameter to account for the effects of both slab thickness and TI. Such a parameter is the minimal flow velocity, $V_{min}$, needed to guarantee complete outflow from an entire slab of slices during TI, which can be expressed as:

$$V_{min}=(Ns+(N-1)d)/(gTI) \quad [2]$$

where s and d are the slice thickness and the interslice distance respectively (s=2 mm and d=0 in the tests discussed above), and g is the scaling factor for a slab-selection gradient applied to prevent an incomplete inversion for the edge slices. The coefficient 1/g means an effective thickening of a slab relative to the standard thickness calculated by the full width at half maximum. For the hyperbolic-secant inversion pulse used in the pulse sequence of the current invention, this factor was determined for g=0.52 to guarantee the correspondence of an inverted slab to a flat top of the excitation profile. The calculated values of $V_{min}$ are given in Table 1, supra. As seen from Table 1, good flow suppression was achieved for $V_{min}$ limited to approximately 12 cm/s. This value is at least two-times less than the typical flow velocity in carotid arteries, which is about 25-110 cm/s, and it probably can be used as an empirical boundary for the design of multi-slice DIR protocols for carotid imaging, which may utilize different N, TR, TI, and slice thickness. It was also noted that the efficiency of flow suppression depends on individual flow patterns, and one may expect poorer suppression when slow flow or re-circulation occurs.

An important practical aspect of the described method is the decrease of the signal from stationary tissues with an increase of N. This effect is essential for image quality in thin-slice, high-resolution imaging of a vessel wall, although it may be less critical in applications with generally high SNR. Saturation of stationary tissues in multi-slice DIR imaging has two origins, which are the effect of the multi-echo (i.e., FSE) sequence and the effect of double inversions. The first effect is well known and can be attributed to off-resonance magnetization transfer and slice cross-talk. The relative role of this kind of saturation is indicated in images obtained using the multi-slice FSE sequence without DIR preparation (see FIGS. 2 and 4, and Table 1). The contribution of cross-talk can be reduced by using an appropriate inter-slice distance, although a potential increase of flow sensitivity may occur due to an increase of thickness of a re-inverted slab (see Eq. [2]). The second saturation mechanism is specifically related to the multi-slice DIR technique, where the frequently repeated double inversions deliver extra saturation to stationary tissues. Comparison between the scans obtained with DIR and pre-saturation for N=8 (Table 1) shows that the inversion pulses are responsible for about half of the total signal loss. As has been shown, a DIR pulse pair is capable of producing a significant saturation effect that is dependent on TI. This effect is especially critical for tissues, as it is caused mainly by on-resonance magnetization transfer. Practically, the specific saturation due to double inversions is negligible at the long TI typically used for $PD/T_2$-weighted single-slice DIR imaging. However, this effect becomes an important limiting factor for the multi-slice DIR technique, when TI is reduced. If high-resolution images of carotid arteries need to be obtained with high SNR for precise evaluation of tissue components relating to the formation of atherosclerotic plaque, the overall image quality required may constrain the available number of slices per TR even more strictly than outflow effects. It was determined that N=4 is optimal (FIGS. 2-5) for clear visualization of the vessel wall for both PD- and $T_2$-weighted images when using the method and hardware of this invention, as described above.

While the only application of the multi-slice DIR method demonstrated is for the high-resolution imaging of carotid arteries, this method potentially can be applied in any area, where efficient flow suppression is required. However, special tests need to be performed for different anatomic regions, since the effectiveness of multi-slice DIR depends on both scan parameters and an actual flow velocity. An application of particular interest could be cardiac imaging, where cardiac gating is absolutely necessary. Non-gated acquisition was used in the present study, because this technique provided excellent blood suppression and image quality without gating. Gating, however, may limit a potential time performance of this method, because the time interval TR/N (see FIG. 1) cannot be shorter than one cardiac cycle (RR interval), if the acquisition for each slice corresponds to the same cardiac phase. In such a situation, a benefit of the multi-slice method could be the acquisition of 2-4 slices per cardiac phase instead of only one slice as is possible with conventional DIR.

In summary, the new multi-slice DIR method of this invention provides a tradeoff between the quality of flow suppression specific for single-slice DIR and the time efficiency of multi-slice FSE with inflow saturation. Just as is true in conventional single-slice DIR, the present technique improves blood suppression significantly with respect to the inflow saturation method. At the same time, a 2-8-fold decrease in the scan time can be obtained with multi-slice DIR relative to single-slice DIR. Based on the discussed properties of the multi-slice DIR method, two strategies have been contemplated for its further clinical applications in carotid imaging. Due to more reliable flow suppression, multi-slice DIR with a relatively large value of N=5-8 can be used instead of inflow-saturated FSE for screening purposes, such as evaluation of an obstructed lumen within a long segment of a carotid artery. For obtaining high-resolution images with high SNR, which are necessary for precise identification of plaque components and morphologic measurements, the technique can be applied with a reduced value of N (i.e., N=2-4) and still be much faster than single-slice DIR.

System for Implementing the Present Invention

Figure 6:
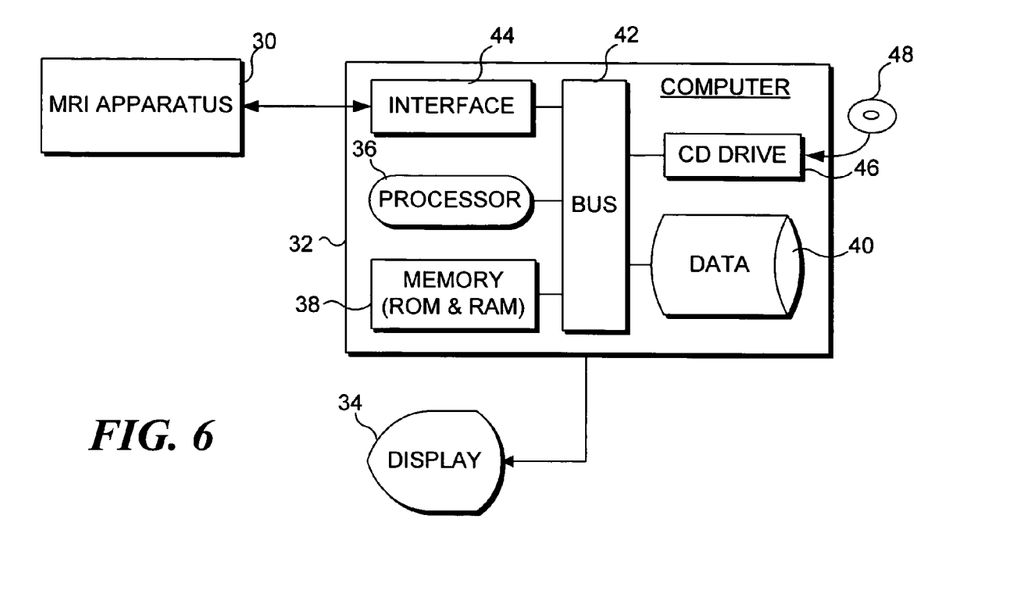
FIG. 6 is a functional block diagram showing a computer coupled to an MRI apparatus, for controlling the MRI apparatus so as to implement the steps of the method for the present invention.

FIG. 6 schematically illustrates a system suitable for implementing the present invention. The system includes a generally conventional MRI apparatus 30 that is controlled by a computer 32. Computer 32 may be a generally conventional personal computer (PC) or a dedicated controller specifically intended for controlling MRI apparatus 30. Although not specifically shown, MRI apparatus 30 includes a magnet to create a permanent magnetic field, a plurality of gradient coils to produce spatial variations of magnetic field, and an RF transceiver and receiver systems to transmit and receive RF signals to and from a plurality of RF coils, as will be well known to those of ordinary skill in the art of MRI. Accordingly, details of the MRI apparatus need not be specifically illustrated or discussed herein.

Computer 32 is coupled to a display 34, which is used for displaying MRI images of slices to an operator. Included within computer 32 is a processor 36. A memory 38 (with both read only memory (ROM) and random access memory (RAM)), a storage 40 (such as a hard drive or other non-volatile data storage device) for storage of data, digital signals, and software programs, an interface 44, and a compact disk (CD) drive 46 are coupled to processor 36 through a bus 42. CD drive 46 can read a CD 48 on which machine instructions are stored for implementing the present invention and other software modules and programs that may be run by computer 32. The machine instructions are loaded into memory 38 before being executed by processor 36 to carry out the steps of the present invention.

Operation of MRI apparatus 30 is controlled by computer 32 when processor 36 executes the machine instructions stored in memory 38. These machine instructions cause the processor to implement the pulse sequence using a DIR procedure and other pulses that are applied in the method. The selective inversion RF pulse is applied to all of the slices comprising a slab. In this pulse sequence, each DIR is followed by the acquisition of a signal for imaging a slice of the slab, e.g., using FSE, followed by a PAD interval, before being repeated, as discussed above, to acquire the signal for imaging each successive slice. The resulting signals for imaging each slice are optionally stored on storage 40 so that selected slices can be displayed on display 34, or our directly displayed. It is also noted that the machine instructions will cause processor 36 to determine the appropriate PAD interval, based upon the TI and number of slices to be imaged per slab, so as to ensure that the blood magnetization is passing through or approaching zero when the signal for imaging each successive slice is acquired.

Steps for Imaging Atherosclerotic Plaque

Figure 7:
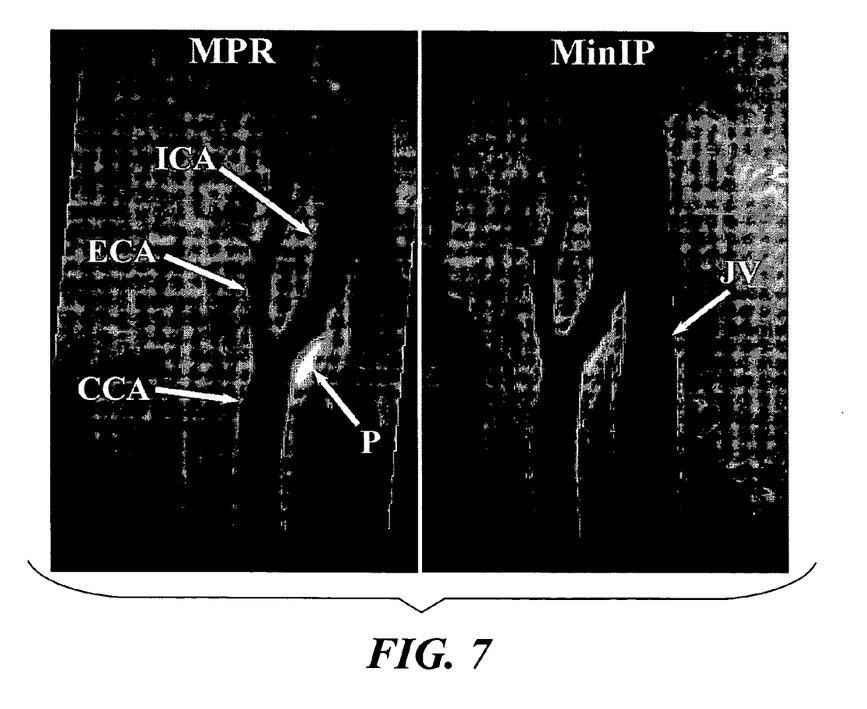
FIG. 7 illustrates oblique black-blood angiographic images processed by multi-planar reformation (MPR—left image) and minimal-intensity projection (MinIP—right image) that were obtained from a patient with moderate atherosclerotic disease and which clearly show the common carotid artery (CCA), internal carotid artery (ICA), end external carotid artery (ECA), jugular vein (JV), and atherosclerotic plaque (P), which does not cause lumen obstruction, as evident in the MinIP image.

As already indicated, while not limited to any specific application, the present invention is particularly useful for improving the visualization of atherosclerotic plaque in a vessel, such as in the carotid artery of a patient, since such plaque and the morphological condition of the plaque are much more readily apparent when the contribution of flowing blood in the artery has been suppressed by employing this invention during the acquisition of the signals used for displaying the MRI images. In an exemplary protocol that uses the present invention, seven imaging sequences are performed. The first two imaging sequences are employed to locate bilateral carotid bifurcations. The third sequence is an oblique black-blood angiographic sequence that uses the improved black-blood imaging of the present invention to precisely determine a position of the bifurcations, which then serve as an index landmark for subsequent transverse imaging sequences, i.e., for transverse imaging sequences 4-7 in which imaged slices are in planes that are generally transverse to the longitudinal direction of the vessel. The third imaging sequence is also helpful for visualizing any plaque distribution, P, along the carotid arteries (i.e., CCA, ICA, ECA), as seen in FIG. 7, and to select one side as an index side. If desired or necessary, the remaining sequences 4-7 can be repeated on the other side.

The four subsequent transverse imaging sequences provide black-blood images with basic contrast weightings. For example, these final four sequences can be done with $T_1$ weighting, PD weighting, and $T_2$ weighting, as well as to produce bright-blood (three dimensional time-of-flight) images, to more clearly characterize plaque and better visually disclose the morphological condition of the plaque. In order to facilitate further comparisons, coverage of transverse imaging sequences 4-7 is prescribed so that slices obtained from different sequences are positioned at about the same distance from the carotid bifurcation of the index side (and optionally, if the other side is to be imaged, the bifurcation on the other side). Using this technique, it is possible to identify one or more morphological conditions of the plaque, including: (a) presence of a lipid core; (b) existence of an intraplaque hemorrhage; (c) necrosis; (d) presence of calcified tissue; and (e) identification of a ruptured fibrous cap on the atherosclerotic plaque.

Although this invention has been described in connection with the preferred form of practicing it and modifications thereto, those of ordinary skill in the art will understand that many other modifications can be made to the invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for suppressing a contribution from flowing blood to a signal used for magnetic resonance imaging (MRI) of each of a plurality of slices at a site in a patient, within a predefined repetition time, comprising the steps of:
   (a) applying one of a non-selective inversion radio frequency (RF) pulse and a selective inversion RF pulse, followed by the other of the non-selective inversion RF pulse and the selective inversion RF pulse, said selective inversion RF pulse simultaneously inverting a magnetization for all of the plurality of slices to be imaged at the site within the predefined repetition time;
   (b) next, waiting a predefined inversion time calculated as a function of a number of slices to be imaged at the site within the predefined repetition time, wherein the predefined inversion time is determined so that each application of a sequence of RF pulses and magnetic field gradient pulses to read out a signal for imaging each successive selected single slice from the plurality of slices occurs at a time when magnetization of the flowing blood is substantially zero, wherein the signal for imaging each successive selected slice is acquired while the magnetization of the flowing blood is substantially zero for said slice;
(c) next, executing the sequence of RF pulses and magnetic field gradient pulses to read out the signal for imaging and displaying a selected single slice from the plurality of slices;
(d) then, waiting a predefined delay time calculated as a function of the number of slices to be imaged; and
(e) repeating steps (a)-(d) in order to image and display each of the plurality of slices in succession, within the predefined repetition time, thereby enabling a clear visual evaluation of anatomic structures and pathologic tissues of interest in each of the selected single slices for diagnostic purposes, since each successive selected single slice is imaged while the magnetization of the flowing blood is substantially zero.

2. The method of claim 1, further comprising the step of storing the signal read out for each successive slice to enable a discrete image of each successive slice to be displayed.

3. The method of claim 1, wherein the predefined delay time is determined so that the sequence of RF pulses and magnetic field gradient pulses are applied to read out the signal for imaging each selected single slice at a time when magnetization of the flowing blood is substantially zero.

4. The method of claim 1, wherein the sequence of RF pulses and magnetic field gradient pulses executed to read out the signal for imaging comprises a fast spin-echo sequence.

5. The method of claim 1, wherein said selective inversion RF pulse and said non-selective inversion RF pulse are adiabatic inversion RF pulses.

6. The method of claim 1, wherein said non-selective inversion RF pulse is a rectangular pulse.

7. The method of claim 1, wherein step (c) begins in synchronization with a selected phase of a cardiac cycle of the patient.

8. The method of claim 1, wherein the plurality of slices includes at least one artery conveying the flowing blood through the site.

9. A memory medium on which machine executable instructions are stored for carrying out the steps of claim 1.

10. A method for multi-slice double inversion-recovery black-blood imaging for a patient, comprising the steps of:
(a) carrying out a double inversion-recovery procedure that includes the step of applying in rapid succession and without regard to order, a non-selective inversion radio frequency (RF) pulse and a selective inversion RF pulse, said selective inversion RF pulse being targeted to act on a slab comprising a plurality of slices;
(b) next, waiting a predefined inversion time calculated as a function of a number of slices to be imaged at the site during a predefined repetition time, wherein the predefined inversion time is determined so that each application of a sequence of RF pulses and magnetic field gradient pulses to read out a signal for imaging each successive selected single slice from the plurality of slices occurs at a time when magnetization of the flowing blood is substantially zero, wherein the signal for imaging each successive selected slice is acquired while the magnetization of the flowing blood is substantially zero for said slice;
(c) next, executing the sequence of RF pulses and magnetic field gradient pulses targeted at one slice in said slab in order to acquire a signal for use in displaying an image of said one slice, wherein a contribution to said image from flowing blood is substantially suppressed and wherein tissue surrounding the flowing blood is consistently visible in the image, thereby aiding evaluation of anatomic structures and pathologic tissues of interest in the one slice;
(d) then waiting a predefined post-signal acquisition delay time; and
(e) repeating steps (a)-(d) for each successive slice comprising the slab, until signals have been acquired for all of the plurality of slices comprising the slab during a predefined repetition time, so that suppression of the contribution from flowing blood to the image of each of the successive slices comprising the slab is achieved, thereby aiding the evaluation of anatomic structures and pathologic tissues of interest in each of the successive slices comprising the slab.

11. The method of claim 10, wherein the post-signal acquisition delay time is determined so that magnetization of flowing blood is substantially zero at a time when the signal is acquired for use in producing the image of each successive slice.

12. The method of claim 10, wherein the predefined inversion time and the post-signal acquisition delay time are determined so that magnetization of flowing blood is approaching zero at a time when the signal is acquired for use in producing the image of each successive slice.

13. The method of claim 10, wherein the plurality of slices are disposed at a location in a patient's body where the flowing blood is flowing through at least one artery.

14. The method of claim 10, further comprising the step of displaying a discrete image for a selected slice from the plurality of slices for which signals were acquired, using the signal that was acquired for the selected slice.

15. The method of claim 14, wherein the sequence of RF pulses and magnetic field gradient pulses targeted at one slice in said slab comprises a fast spin-echo sequence.

16. The method of claim 14, wherein said selective inversion RF pulse and said non-selective inversion RF pulse are adiabatic inversion RF pulses.

17. The method of claim 14, wherein said non-selective inversion RF pulse is a rectangular pulse.

18. The method of claim 14, wherein step (c) begins in synchronization with a selected phase of a cardiac cycle of the patient.

19. The method of claim 10, wherein the plurality of slices are imaged for each cardiac cycle of a patient.

20. A memory medium on which machine executable instructions are stored for carrying out the steps of claim 10.

21. A controller for generating a pulse sequence for multi-slice double inversion-recovery magnetic resonance imaging, said pulse sequence being repeated for acquiring a signal usable to image each of a succession of slices included in a slab, comprising:
(a) a memory in which a plurality of machine executable instructions are stored; and
(b) a processor that is coupled to the memory and executes the machine executable instructions causing the pulse sequence to be generated, said pulse sequence being characterized by including:
(i) a double inversion pulse pair generated to include in rapid succession, but without regard to order, a non-selective inversion radio frequency (RF) pulse and a slab-selective inversion RF pulse targeted at a slab comprising a plurality of slices;
(ii) an inversion delay period calculated as a function of a number of slices to be imaged at the site, wherein the inversion delay period is determined so that during use of the pulse sequence, magnetization of the flowing blood is substantially zero at a time when the acquisition sequence of RF pulses and magnetic field gradient pulses are applied to read out the signal usable for producing an image of each successive slice of the slab, wherein the signal for imaging each successive slice is acquired while the magnetization of the flowing blood is substantially zero for said slice;

(iii) an acquisition sequence of RF pulses and magnetic field gradient pulses generated and applied for spatial encoding and read out of a signal usable for producing an image of a slice; and (iv) a post-signal acquisition delay period that is applied before the pulse sequence is repeated to acquire a signal for imaging a successive slice of the slab and for displaying an image of the successive slice of the slab in order to aid in visually evaluating anatomic structures and pathologic tissues of interest.

22. The controller of claim 21, wherein the post-acquisition delay period is determined so that during use of the pulse sequence, magnetization of flowing blood is substantially zero at a time when the acquisition sequence of RF pulses and magnetic field gradient pulses are applied to read out the signal usable for producing the image of each successive slice of the slab.

23. The controller of claim 21, wherein the inversion delay period and the post-acquisition delay period are determined so that during use of the pulse sequence, the magnetization of flowing blood is approaching zero at a time when the acquisition sequence of RF pulses and magnetic field gradient pulses are applied to read out the signal usable for producing the image of each successive slice of the slab.

24. The controller of claim 21, wherein the inversion delay period is determined as a function of a number of slices in the slab that are to be imaged during a predefined repetition time.

25. The controller of claim 21, wherein the acquisition sequence of RF pulses and magnetic field gradient pulses comprises a fast spin-echo sequence.

26. The controller of claim 21, wherein said slab-selective inversion RF pulse and said non-selective RF pulse are adiabatic inversion RF pulses.

27. The controller of claim 21, wherein the said non-selective inversion RF pulse is a rectangular pulse.

28. The controller of claim 21, wherein said pulse sequence is synchronized with a cardiac rhythm of a patient to whom the pulse sequence is applied.

29. A system for multi-slice double inversion-recovery black-blood imaging, comprising:

(a) an MRI apparatus adapted for producing an image of a site; and (b) a computer coupled to the MRI apparatus to control it, said computer including:

(i) a memory in which machine instructions are stored; and (ii) a processor coupled to the memory, said processor executing the machine instructions to control the MRI apparatus to carry out a sequence of operations, including:

(1) carrying out a double inversion-recovery procedure that includes the step of applying in rapid succession and without regard to order, a non-selective inversion radio frequency (RF) pulse and a selective inversion RF pulse, said selective inversion RF pulse being targeted to act on a slab comprising a plurality of slices;

(2) next, waiting a predefined inversion time calculated as a function of a number of slices to be imaged at the site during the predefined repetition time, determined so that magnetization of flowing blood is substantially zero at each successive time when the signal is acquired for use in producing an image of a successive slice, wherein the signal for imaging each successive slice is acquired while the magnetization of the flowing blood is substantially zero for said slice;

(3) next, executing a sequence of RF pulses and magnetic field gradient pulses targeted at one slice in said slab in order to acquire a signal for use in producing an image of said one slice, wherein a contribution to said image from flowing blood is substantially suppressed and wherein tissue surrounding the flowing blood is consistently visible in the image;

(4) then, waiting a predefined post-signal acquisition delay time; and (5) repeating steps (1)-(4) for each successive slice comprising the slab, until signals have been acquired for all of the plurality of slices comprising the slab during a predefined repetition time.

30. The system of claim 29, wherein the post-signal acquisition delay time is determined so that magnetization of flowing blood is substantially zero at a time when the signal is acquired for use in producing the image of each successive slice.

31. The system of claim 29, wherein the predefined inversion time and the post-signal acquisition delay time are determined so that magnetization of flowing blood is approaching zero at a time when the signal is acquired for use in producing the image of each successive slice.

32. The system of claim 29, further comprising a display coupled to the processor, wherein the machine instructions further cause the processor to display a discrete image for a selected slice from the plurality of slices for which signals were acquired, using the signal that was acquired for the selected slice.

33. The system of claim 29, wherein the machine instructions further cause the processor to image a plurality of slices for each cardiac cycle of a patient with which the system is used.

34. A method for enabling visual evaluation of atherosclerotic plaque in a blood vessel of a patient, comprising the steps of:

(a) identifying a plurality of slices to be imaged at a site, said plurality of slices being within a plane that is generally transverse to a longitudinal direction of the blood vessel;

(b) applying to the site one of a non-selective inversion radio frequency (RF) pulse and a selective inversion RF pulse, followed by the other of the non-selective inversion RF pulse and the selective inversion RF pulse, said selective inversion RF pulse simultaneously inverting a magnetization for all of the plurality of slices to be imaged at the site;

(c) next, waiting a predefined inversion time calculated as a function of a number of slices to be imaged at the site within a predefined repetition time, said predefined inversion time being determined so that the sequence of RF pulses and magnetic field gradient pulses are applied to read out the signal for imaging each selected single slice at each successive time when a magnetization signal for the flowing blood is substantially zero, wherein the signal for imaging each successive selected slice is acquired while the magnetization of the flowing blood is substantially zero for said slice;

(d) next, executing a sequence of RF pulses and magnetic field gradient pulses to read out a signal for imaging a selected single slice from the plurality of slices;

(e) next, waiting a predefined delay time calculated as a function of the number of slices to be imaged;

(f) repeating steps (b)-(e) to image each of the plurality of slices at the site in succession, within the predefined repetition time; and (g) displaying selected slice images of the site, any atherosclerotic plaque in an artery of the patient at the site being clearly visible in the transverse slice images that are displayed, a contribution due to flowing blood being suppressed to more clearly visually display such atherosclerotic plaque in the artery.

35. The method of claim 34, wherein the step of identifying the plurality of slices to be imaged comprises the step of determining an index location for use as a reference when imaging the plurality of slices.

36. The method of claim 34, further comprising the step of acquiring a signal with at least one type of contrast weighting when carrying out the step of reading out the signal.

37. The method of claim 36, wherein said at least one type of contrast weighting comprises at least one of a $T_1$ weighting, a proton density (PD) weighting, and a $T_2$ weighting.

38. The method of claim 34, wherein the predefined delay time is determined so that the sequence of RF pulses and magnetic field gradient pulses are applied to read out the signal for imaging each selected single slice at a time when a magnetization signal for the flowing blood is substantially zero.

39. The method of claim 34, wherein the step of displaying selected slices of the site enable visualization of one or more morphological conditions of any atherosclerotic plaque at the site, including:
  (a) a lipid core in the atherosclerotic plaque;
  (b) an intraplaque hemorrhage in the atherosclerotic plaque;
  (c) necrosis in the atherosclerotic plaque;
  (d) calcified tissue within the atherosclerotic plaque; and
  (e) a ruptured fibrous cap on the atherosclerotic plaque.

40. The method of claim 34, wherein the step of identifying the plurality of slices to be imaged at the site comprises the steps of:
  (a) to the site of the blood vessel, applying one of a non-selective inversion radio frequency (RF) pulse and a selective inversion RF pulse, followed by the other of the non-selective inversion RF pulse and the selective inversion RF pulse, said selective inversion RF pulse simultaneously inverting a magnetization for all of an initial plurality of slices to be imaged within the predefined repetition time;
  (b) next, waiting a predefined inversion time that is calculated as a function of a number of slices to initially be imaged at the site within the predefined repetition time;
  (c) next, executing a sequence of RF pulses and magnetic field gradient pulses to read out a signal for imaging a selected single slice from the plurality of slices to initially be imaged;
  (d) then, waiting a predefined delay time calculated as a function of the number of slices to initially be imaged;
  (e) repeating steps (a)-(d) to image each of the initial plurality of slices in succession, within the predefined repetition time; and
  (f) processing signals read out to display images of slices initially imaged at the site, said images being used to further identify the position of the transverse slices.

41. A method for black-blood angiography that enables visualization of blood vessels and lesions formed inside the blood vessels of a patient, comprising the steps of:
  (a) identifying a plurality of slices to be imaged at a site within the patient, said plurality of slices being within a plane that is generally oblique to a longitudinal direction of the blood vessel;
  (b) applying to the site one of a non-selective inversion radio frequency (RF) pulse and a selective inversion RF pulse, followed by the other of the non-selective inversion RF pulse and the selective inversion RF pulse, said selective inversion RF pulse simultaneously inverting a magnetization for all of the plurality of slices to be imaged at the site;
  (c) next, waiting a predefined inversion time calculated as a function of a number of slices to be imaged at the site within a predefined repetition time, said predefined inversion time being determined so that a sequence of RF pulses and magnetic field gradient pulses are applied to read out the signal for imaging a successive selected single slice at each successive time when a magnetization signal for the flowing blood is substantially zero, wherein the signal for imaging each successive selected slice is acquired while the magnetization of the flowing blood is substantially zero for said slice;
  (d) next, executing a sequence of RF pulses and magnetic field gradient pulses to read out a signal for imaging a selected single slice from the plurality of slices;
  (e) next, waiting a predefined delay time calculated as a function of the number of slices to be imaged;
  (f) repeating steps (b)-(e) to image each of the plurality of slices at the site in succession, within the predefined repetition time; and
  (g) processing the plurality of slice images by an algorithm, producing an image displaying continuity of blood vessels so that the blood vessels are consistently dark, in contrast to tissue outside the blood vessels and any lesions inside the blood vessels.

42. The method of claim 41, wherein the algorithm of the step (g) comprises multiplanar reformation.

43. The method of claim 41, wherein the algorithm of the step (g) comprises minimal intensity projection.

44. The method of claim 41, wherein any lesion inside the blood vessel comprises one of an atherosclerotic plaque and a thrombus.

* * * * *

UNITED STATES PATENT AND TRADEMARK OFFICE
CERTIFICATE OF CORRECTION

PATENT NO. : 7,315,756 B2  
APPLICATION NO. : 10/788937  
DATED : January 1, 2008  
INVENTOR(S) : V. L. Yarnykh et al.

It is certified that error appears in the above-identified patent and that said Letters Patent is hereby corrected as shown below:

In the Specification

| Column | Line | |
|---|---|---|
| 1 | 15 | Delete the text under GOVERNMENT RIGHTS, and insert: --This invention was made with government support under Grant No. HL056874, awarded by the National Institutes of Health. The government has certain rights in the invention.-- |

Signed and Sealed this  
Twenty-eighth Day of April, 2020

Andrei Iancu  
*Director of the United States Patent and Trademark Office*